United States Patent [19]
Kondo et al.

[11] Patent Number: 4,946,941
[45] Date of Patent: Aug. 7, 1990

[54] NOVEL GLYCOPEPTIDE ANTIBIOTICS

[75] Inventors: Eiji Kondo, Osaka; Naoki Tsuji, Hyogo; Koichi Matsumoto, Osaka; Yoshimi Kawamura, Osaka; Tadashi Yoshida, Osaka; Shinzo Matsuura, Hyogo, all of Japan

[73] Assignee: Shionogi & Co., Ltd., Osaka, Japan

[21] Appl. No.: 3,252

[22] Filed: Jan. 14, 1987

[30] Foreign Application Priority Data

Jan. 24, 1986 [JP] Japan .................................. 61-14389
Aug. 11, 1986 [JP] Japan ................................ 61-188865

[51] Int. Cl.$^5$ ........................... C07K 7/64; C07K 9/00
[52] U.S. Cl. ..................................... 530/317; 530/322; 435/71.3
[58] Field of Search ................................. 530/317, 322

[56] References Cited

U.S. PATENT DOCUMENTS

| | | | |
|---|---|---|---|
| 4,495,179 | 1/1985 | Hoehn et al. | 530/322 |
| 4,547,488 | 10/1985 | Merkel | 530/322 |
| 4,717,714 | 1/1988 | Boeck et al. | 530/317 |
| 4,804,534 | 2/1989 | Riva et al. | 424/118 |

Primary Examiner—Lester L. Lee
Attorney, Agent, or Firm—Wenderoth, Lind & Ponack

[57] ABSTRACT

The compounds of the formula:

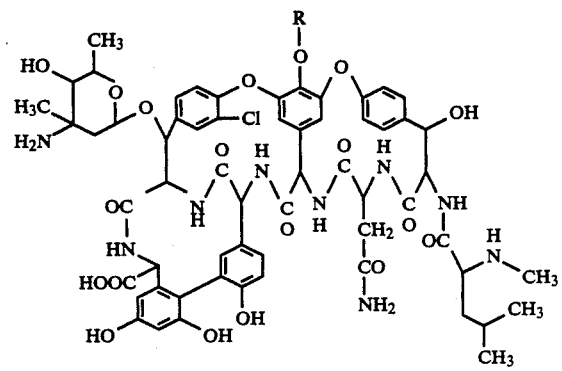

wherein R is

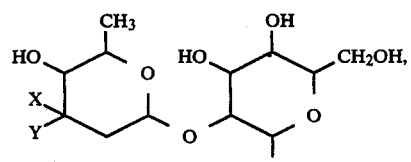

or

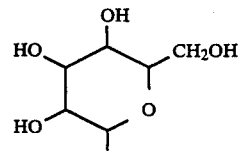

or H, wherein X is $NH_2$ and Y is $CH_3$; or X is OH and Y is H, and their pharmaceutically acceptable salts. The compounds have a potent activity against gram-positive bacteria, especially, methicillin-resistant bacteria.

5 Claims, 8 Drawing Sheets

NOVEL GLYCOPEPTIDE ANTIBIOTICS

BACKGROUND OF THE INVENTION (1) Field of the Invention

This invention relates to glycopeptide antibiotics represented by the following formula I:

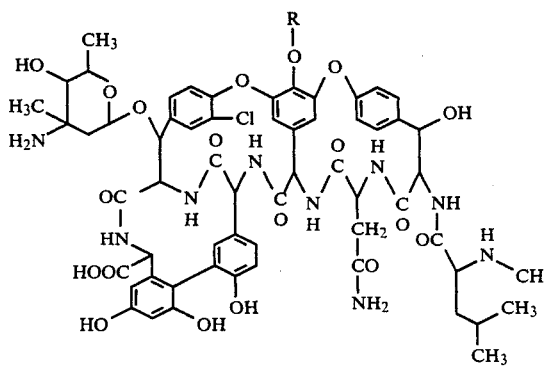

wherein R is

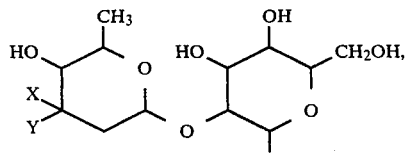

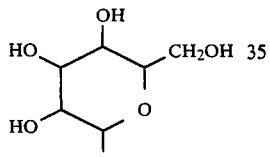

or H, wherein X is $NH_2$ and Y is $CH_3$; or X is OH and Y is H, and its pharmaceutically acceptable salt. This invention further relates to their production and microorganisms producing them.

(2) Description of the Prior Art

Recently, as a lot of antibiotics have generally been used, the emergence of the microorganism resistant against many kinds of antibiotics, especially methicillin-resistant microorganism, has been growing into a severe problem. The methicillin-resistant microorganism is resistant not only against methicillin but also against almost all of antibiotics such as aminoglycosides, tetracyclines, cephalosporins, cephamycins, penems, carbapenems and macrolides.

It has been discovered that glycopeptides, especially vancomycins, show potent activity against said methicillin-resistant microorganisms (Antimicrobial Agents and Chemotherapy 28, 660–662 (1985)). Vancomycin is a well-known antibiotic (Japanese Patent Publication No. 33-8450) and its new analogs have been discovered (Antimicrobial Agents and Chemotherapy 28, 660–662 (1985); The Journal of Antibiotics 37, 446–453 (1984), 38, 1–8 (1985), 38, 51–57 (1985); Japanese Unexamined Patent Publication Nos. 60-39623, 60-199397, 60-231698, 60-237099, and so on). Antibiotics PA-42867-A and PA-42867-B of this invention are new vancomycin antibiotics having different structures from those of the above-mentioned compounds.

Vancomycin now on the market which has low purity has been used as orally administrable preparations and is difficult to apply as injectable preparations. Accordingly, it is desired to explore such an antibiotic having more potent activity against methicillin-resistant microorganisms than conventional Vancomycins.

SUMMARY

The antibiotic represented by the formula I wherein R is

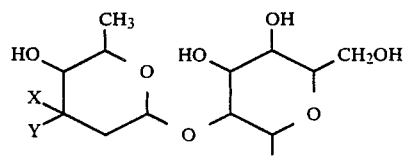

wherein X is $NH_2$ and Y is $CH_3$, is named PA-42867-A. The antibiotic represented by the formula I wherein R is

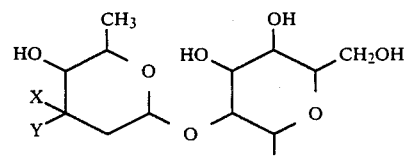

wherein X is OH and Y is H, is named PA-42867-B. The antibiotic represented by the formula I wherein R is

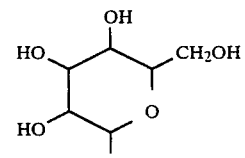

is named des-(4-epi-vancosaminyl)-PA-42867-A. The antibiotic represented by the formula I wherein R is H is named des-(4-epi-vancosaminyl-O-glucosyl)-PA-42867-A.

The PA-42867-A and the PA-42867-B are prepared by fermenting a PA-42867-A- and/or PA-42867-B-producing microorganism belonging to the genus Nocardia in a broth and collecting the PA-42867-A and/or PA-42867-B from the fermented broth. The des-(4-epi-vancosaminyl)-PA-42867-A and the des-(4-epi-vancosaminyl-O-glucosyl)-PA-42867-A are prepared by hydrolyzing the PA-42867-A and/or the PA-42867-B. All of them have a novel structure and present an excellent antibacterial activity against gram positive microorganisms, in particular, methicillin-resistant *Staphylococcus aureus* in vitro and in vivo.

DESCRIPTION OF THE PREFERRED EMBODIMENT

The present inventors have found a strain of the genus Nocardia producing the compounds represented by the following formula II;

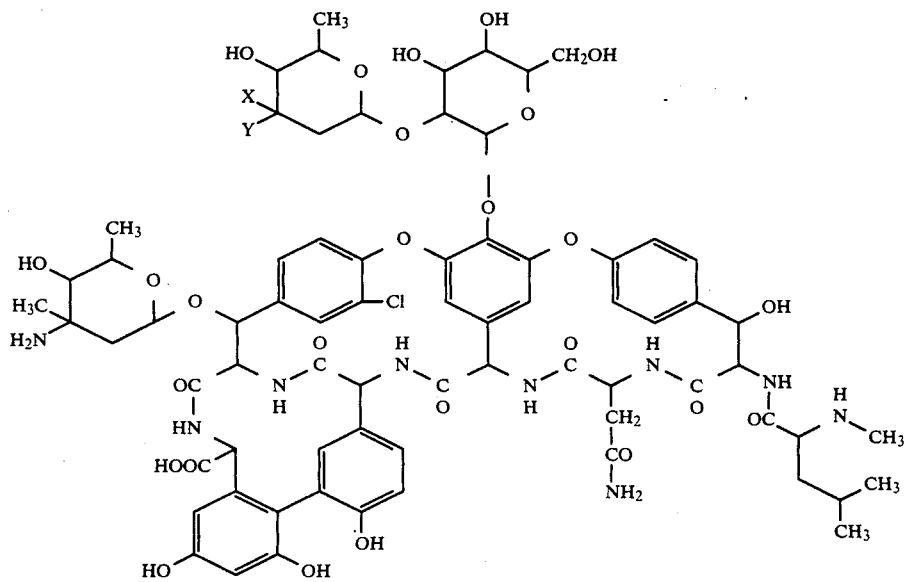

wherein X is $NH_2$ and Y is $CH_3$; or X is OH and Y is H, which shows potent activity against methicillin-resistant microorganism. The compound of the formula II wherein X is $NH_2$ and Y is $CH_3$ was named PA-42867-A and the compound of the formula II wherein X is OH and Y is H was named PA-42867-B. This invention comprehends not only the above two compounds but their pharmaceutically acceptable salts.

The physicochemical properties of the compounds PA-42867-A and PA-42867-B of this invention are shown below.

PHYSICOCHEMICAL PROPERTY

Figure 1:
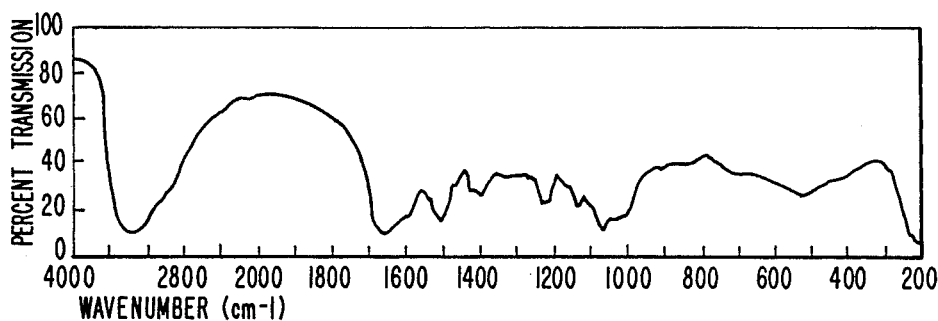
FIG. 1, FIG. 2, FIG. 3 and FIG. 4 show IR spectrum, mass spectrum, $^1$H-NMR spectrum and $^{13}$C-NMR spectrum of PA-42867-A, respectively.
Figure 2:
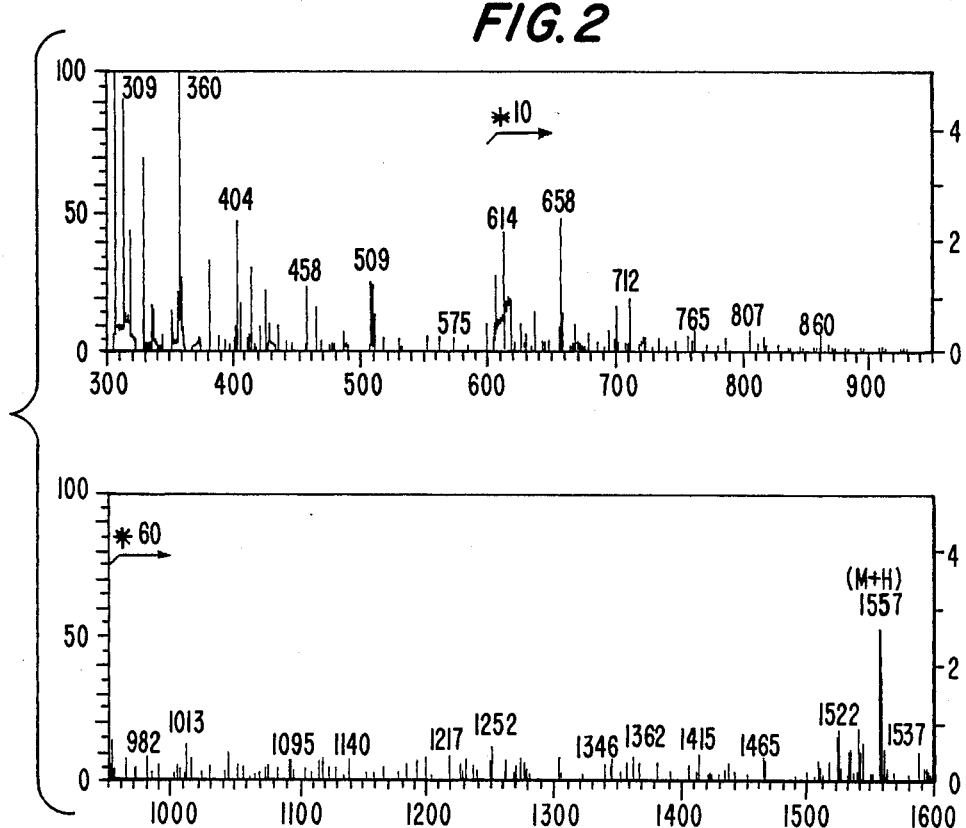
Figure 3:
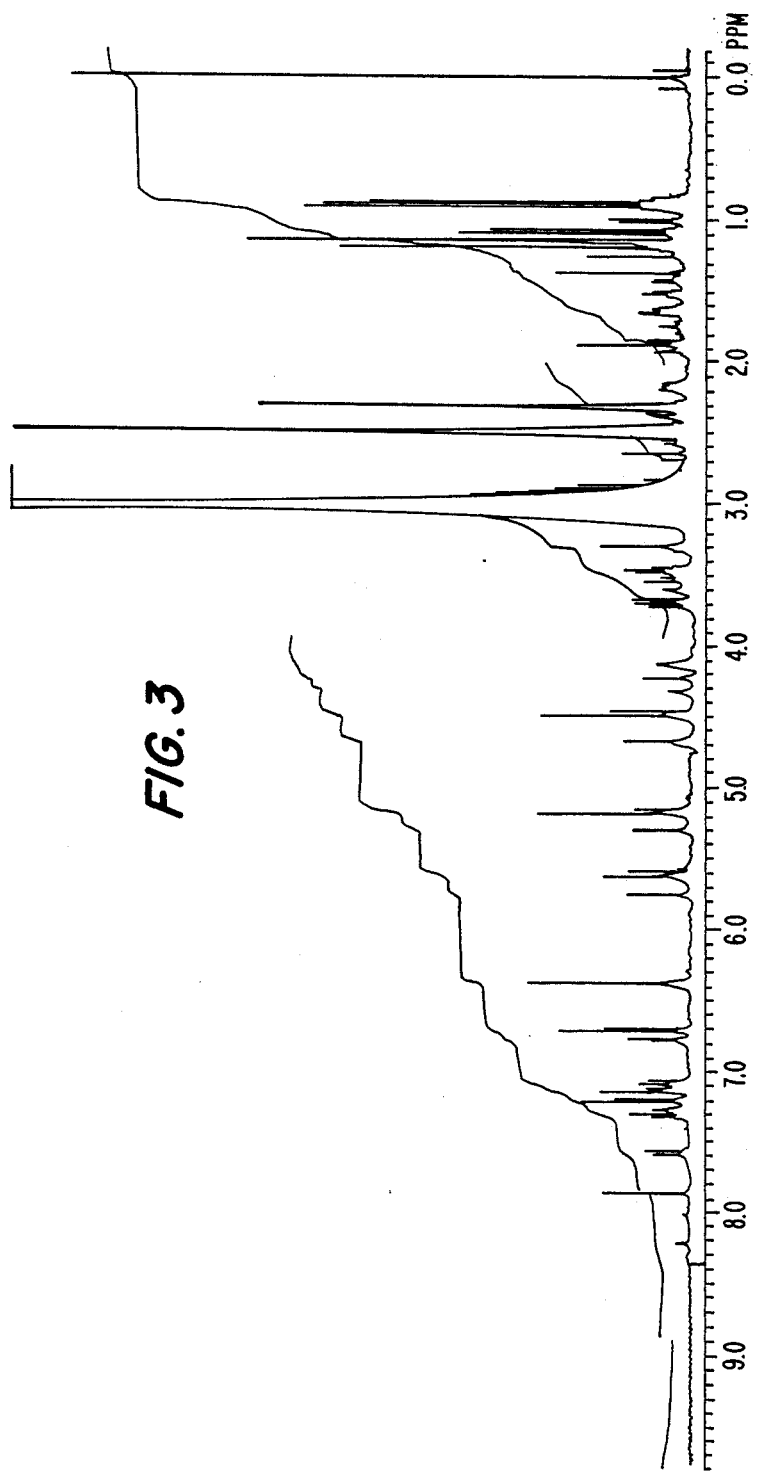

① PA-42867-A
UV spectrum
$\lambda_{max}^{0.01NHCl}$nm($E_{1cm}^{1\%}$): 281.8 (41.15). $\lambda_{max}^{0.01NNaOH.aq}$nm($E_{1cm}^{1\%}$): 302.6 (43.14).
Specific rotatory power
$[\alpha]_D^{25°}$: $-88.8\pm3.1°$ (c=0.41, water).
IR spectrum (see FIG. 1)
IR (KBr): 3396, 1654, 1588(sh), 1505, 1420, 1396, 1223, 1131, 1064, 1010(sh) $cm^{-1}$.
Mass spectrum (see FIG. 2)
MS m/z: 1557 $(M+H)^{30}$.
Anal. calcd. (%) for $C_{73}H_{89}O_{26}N_{10}Cl.3\frac{1}{2}H_2O$ : C;54.08, H;5.97, N;8.64, Cl;2.19. Found (%): C;54.03, H;6.14, N;8.60, Cl;2.19.
NMR spectrum
$^1$H-NMR: 400 MHz, in $d_6$DMSO+1 drop $D_2O$, internal standard TMS, 100° C., (see FIG. 3)
δ ppm: 0.88 (d, 6.5, 3H), 0.917 (d, 6.0, 3H), 1.093 (d, 6.0, 3H), 1.156 (s, 3H), 1.167 (d, 6.2, 3H), 1.202 (s, 3H), around 1.425 (m, 1H), around 1.525 (m, 1H), 1.630 (dd, 13.6, 4.3, 1H), 1.640 (dd, 13.6, 4.3, 1H), 1.766 (m, 1H), 1.866 (d like, 13.6, 1H), 1.915 (d like, 13.6, 1H), 2.175 (dd, 16.0, 7.5, 1H), 2.315 (s, 3H), 2.560 (dd, 16.0, 5.0, 1H), 2.892 (d, 9.5, 1H), 2.947 (d, 9.6, 1H), around 3.03 (shaded by water in solvent, 1H), around 3.31 (m, 2H), 3.428 (t like, around 8.7, 1H), 3.540 (dd, 11.6, 4.8, 1H), 3.609 (qd, 6.2, 9.5, 1H), 3.688 (dd, 7.2, 8.7, 1H), 3.730 (dd, 11.6, 2.1, 1H), 4.141 (qd, 6.0, 9.6, 1H), 4.233 (broad s like, 1H), 4.328 (dd, 5.0, 7.5, 1H), 4.485 (s like, 1H), 4.516 (s, 1H), 4.674 (d like, around 4.3, 1H), 4.699 (d, 4.0, 1H), 5.152 (d like, around 4.0, 1H), 5.188 (broad s like, 1H), 5.190 (s like, 1H), 5.305 (d like, around 4.3, 1H), 5.603 (d, 7.2, 1H), 5.638 (broad s like, 1H), 5.762 (broad s like, 1H), 6.375 (d, 2.3, 1H), 6.388 (d, 2.3, 1H), 6.712 (d, 8.3, 1H), 6.793 (dd, 8.3, 2.2, 1H), 7.087 (dd, 8.5, 2.2, 1H), 7.120 (dd, 8.3, 2.2, 1H), 7.148 (d, 2.2, 1H), 7.215 (d, 8.4, 1H), 7.286 (broad dd like, around 8.3, around 2.0, 1H), 7.327 (dd, 8.4, 2.0, 1H), 7.586 (broad dd like, around 8.5, around 2, 1H), 7.863 (d, 2.0, 1H).

Figure 4:
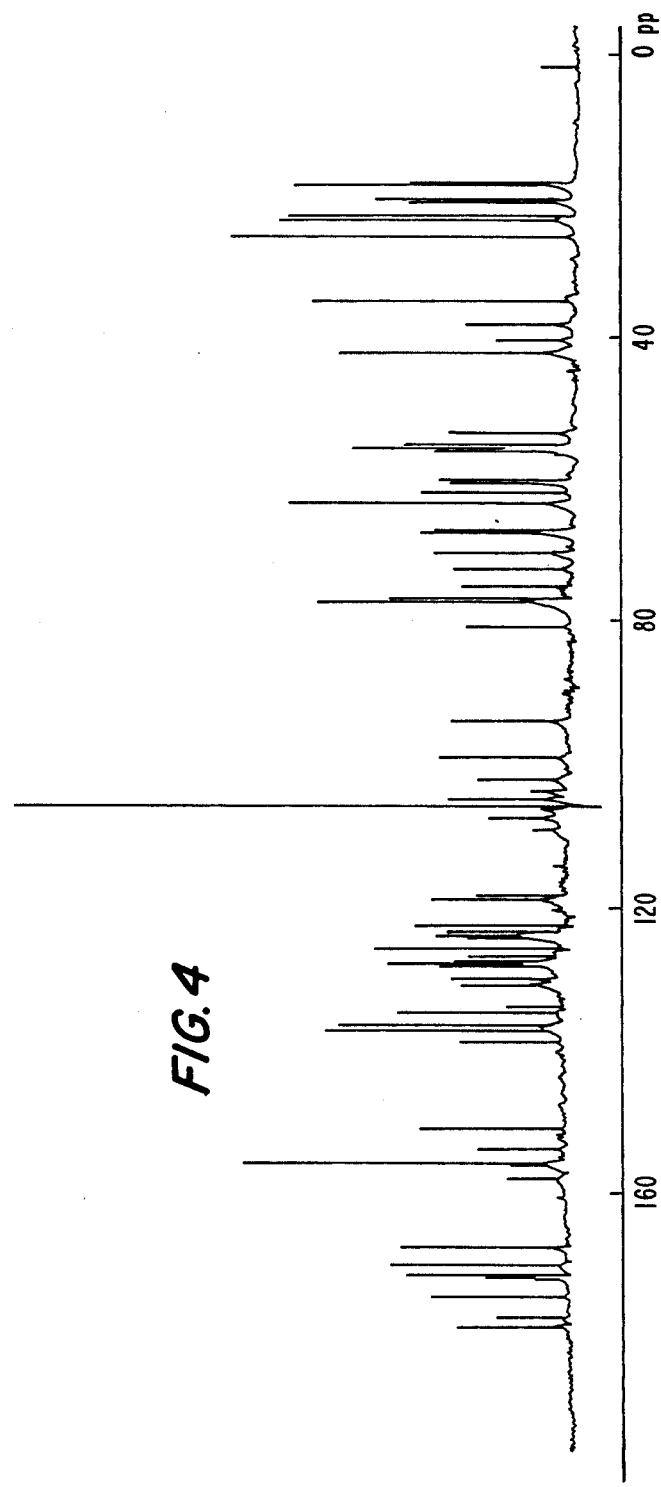

$^{13}$C-NMR: 50 MHz, in $D_2O$, external standard $CH_3CN$ 1.7 ppm, 60° C. (see FIG. 4).
δ ppm: 178.9, 177.8, 174.8, 172.1, 171.9, 171.7, 170.3, 167.8, 158.0, 156.3, 155.9, 155.85, 155.85, 153.85, 151, 138.8, 137, 136.85, 136.7, 134.9, 133.9, 131, 130, 128.8, 128.4, 127.8, 127.1, 126.2, 124.6, 124.2, 123.9, 122.8, 119.4, 118.6, 107.4, 107.3, 104.9 104, 102.3, 99.2, 94, 80.7, 77.5 77.5, 76.9, 76.8, 75.2, 72.5, 70.4, 67.4, 67.2, 63.4, 63.4, 61.7, 60.5, 59.9, 56.1, 55.5, 55.5, 54.9, 52.7, 42, 41.4, 39.85, 37.6, 34.9, 25.2, 23.3, 22.5, 20.6, 19.9, 18.4, 18.1.

Thin layer chromatography
Merck precoated TLC plate silica gel 60F254.
Developing solvent: chloroform:methanol:conc. ammonia water:sec-butanol:water (5:10:5:5:2).
Rf=0.28.
High performance liquid chromatography (Shimazu LC-6A)
Column: Chemco Pak Nucleosil 5C18 φ4.6×150 mm (Chemco Scientific Co., Ltd.).
Detection: UV 220 nm.
Flow rate: 1 ml/min.
Mobile phase: 8% acetonitrile-0.05M phosphate buffer (pH3.5).
Retention time: 8.8 min.
Mobile phase: 9% acetonitrile-0.05M phosphate buffer (pH3.5).
Retention time: 5.6 min.
Color reaction: Ninhydrin positive
Solubility Soluble in water and dimethylsulfoxide.
Slightly soluble in alcohol.
Insoluble in ether, benzene, chloroform and ethyl acetate.

Appearance
amphoteric, white amorphous powder

② PA-42867-B

UV spectrum
$\lambda_{max}^{0.01NHCl}$nm($E_{1cm}^{1\%}$): 281.6 (44.22).
$\lambda_{max}^{0.01NNaOH.aq}$nm($E_{1cm}^{1\%}$): 301 (45.94).

Specific rotatory power
$[\alpha]_D^{25°}$: $-97.3\pm3.3°$ (c=0.41, water).

Figure 5:
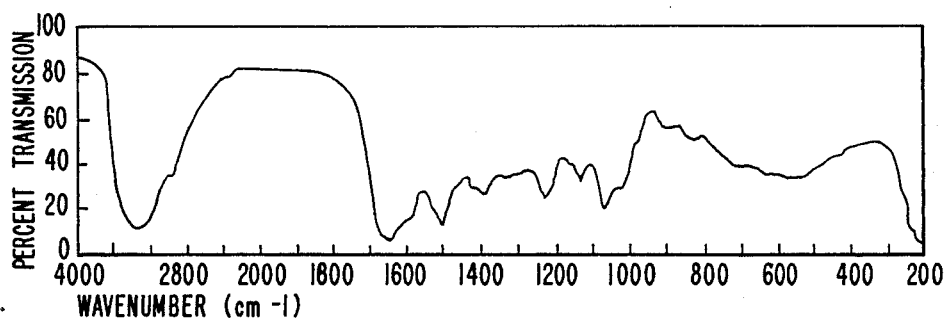
FIG. 5, FIG. 6, FIG. 7 and FIG. 8 show IR spectrum, mass spectrum, $^1$H-NMR spectrum and $^{13}$C-NMR spectrum of PA-42867-B, respectively.

IR spectrum (see FIG. 5)
IR (KBr): 3360, 1656, 1587(sh), 1505, 1421, 1393, 1230, 1129, 1062, 1013(sh) cm$^{-1}$.

Figure 6:
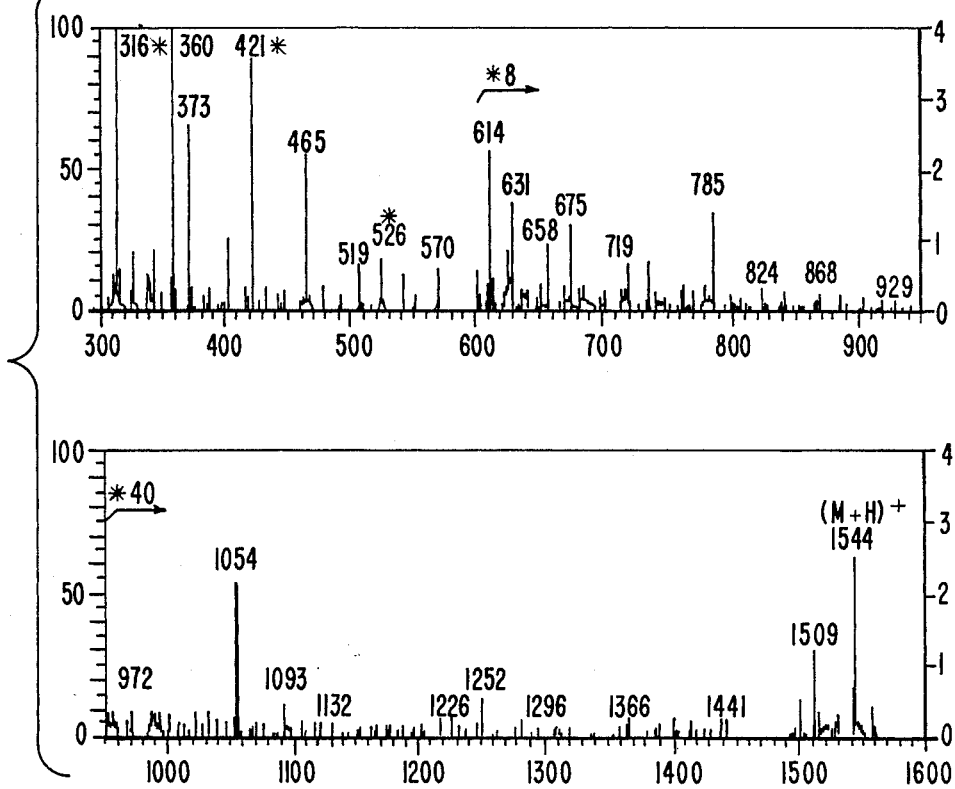

Mass spectrum (see FIG. 6)
MS m/z: 1544 (M+H)$^+$.

Anal. Calcd. (%) for $C_{72}H_{86}O_{27}N_9Cl.1\frac{1}{2}H_2O$ : C;55.01, H;5.71, N;8.02, Cl;2.26. Found (%): C;54.83, H;5.81, N;8.46, Cl;2.13.

Figure 7:
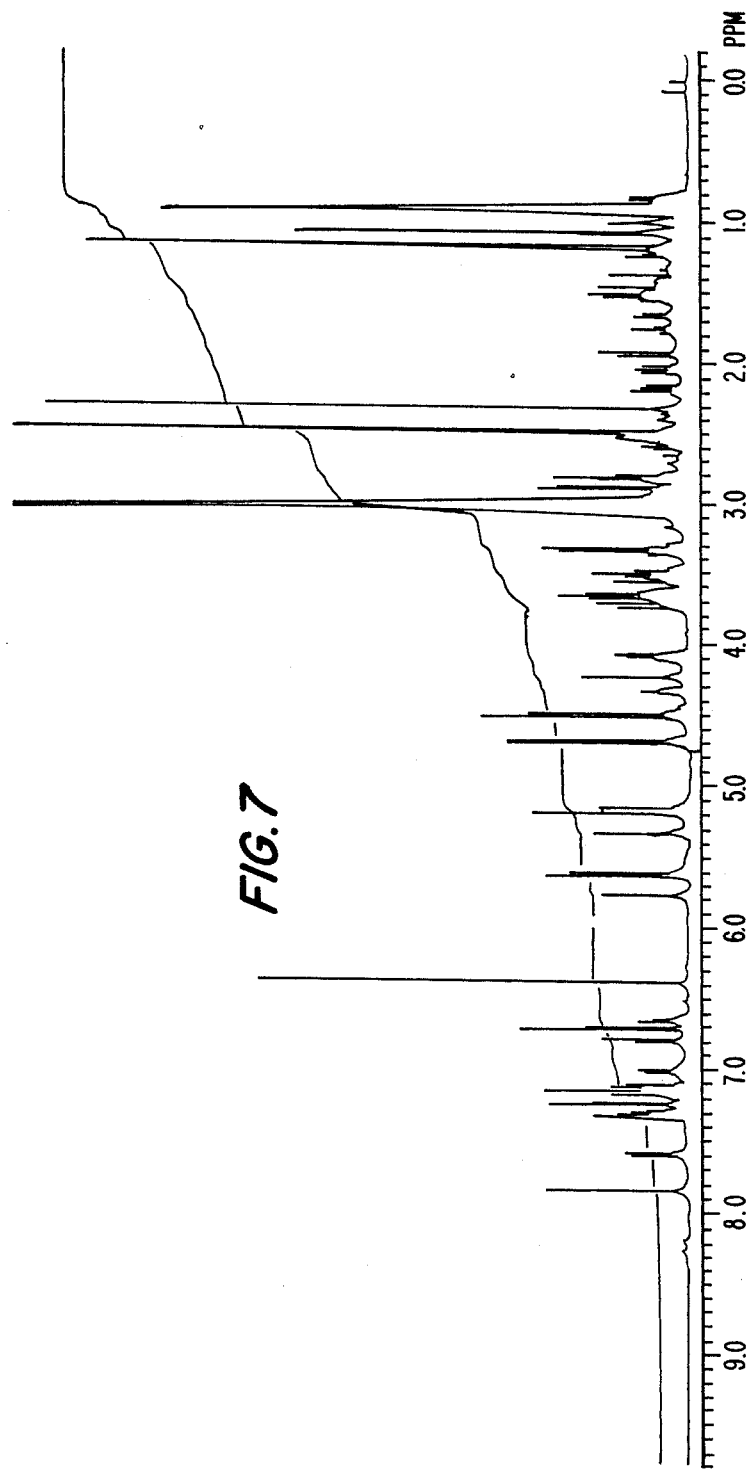

NMR spectrum
$^1$H-NMR: 400 MHz, in d$_6$-DMSO+1 drop D$_2$O, internal standard TMS, 100° C. (see FIG. 7).

δ ppm: 0.891 (d, 6.6, 3H), 0.919 (d, 6.5, 3H), 1.080 (d, 6.2, 3H), 1.159 (s, 3H), 1.173 (d, 6.0, 3H), around 1.428 (m, 1H), 1.469 (m, 1H), around 1.525 (m, 1H), 1.647 (dd, 13.7, 4.4, 1H), 1.767 (m, 1H), 1.920 (d, like, 13.7, 1H), 2.042 (dd like, around 13.0, around 5.3, 1H), 2.182 (dd, 16.0, 7.5, 1H), 2.314 (s, 3H), 2.565 (dd, 16.0, 4.8, 1H), 2.817 (t like, around 9.1, 1H), 2.895 (d, 9.7, 1H), around 3.03 (Shaded by water in solvent, 1H), around 3.33 (m, 2H), 3.497 (t like, around 8.5, 1H), 3.547 (dd, 11.6, 4.9, 1H), 3.636 (qd, 6.0, 9.7, 1H), 3.668 (dd, 7.2, 8.5, 1H), around 3.685 (m, 1H), 3.733 (dd, 11.6, 2.3, 1H), 4.092 (qd, 6.2, 9.3, 1H), 4.234 (br d, around 1.5, 1H), 4.330 (dd, 4.8, 7.5, 1H), 4.489 (s like, 1H), 4.516 (s, 1H), 4.686 (d like, around 4.4, 1H), 4.692 (d, 3.9, 1H), 5.156 (d like, around 3.9, 1H), 5.192 (broad s like, 1H), 5.200 (s like, 1H), 5.334 (d like, around 3.5, 1H), 5.604 (d, 7.2, 1H), 5.641 (broad s like, 1H), 5.771 (broad s like, 1H), 6.388 (s like, 2H), 6.719 (d, 8.5, 1H), 6.800 (dd, 8.5, 2.3, 1H), 7.107 (dd, 8.4, 2.4, 1H), 7.147 (d, 2.3, 1H), 7.170 (dd, 8.4, 2.4, 1H), 7.237 (d, 8.4, 1H), 7.296 (broad dd, around 8.4, around 2.0, 1H), 7.331 (dd, 8.4, 2.0, 1H), 7.590 (broad dd, 8.4, around 2.2, 1H), 7.857 (d, 2.0, 1H)

Figure 8:
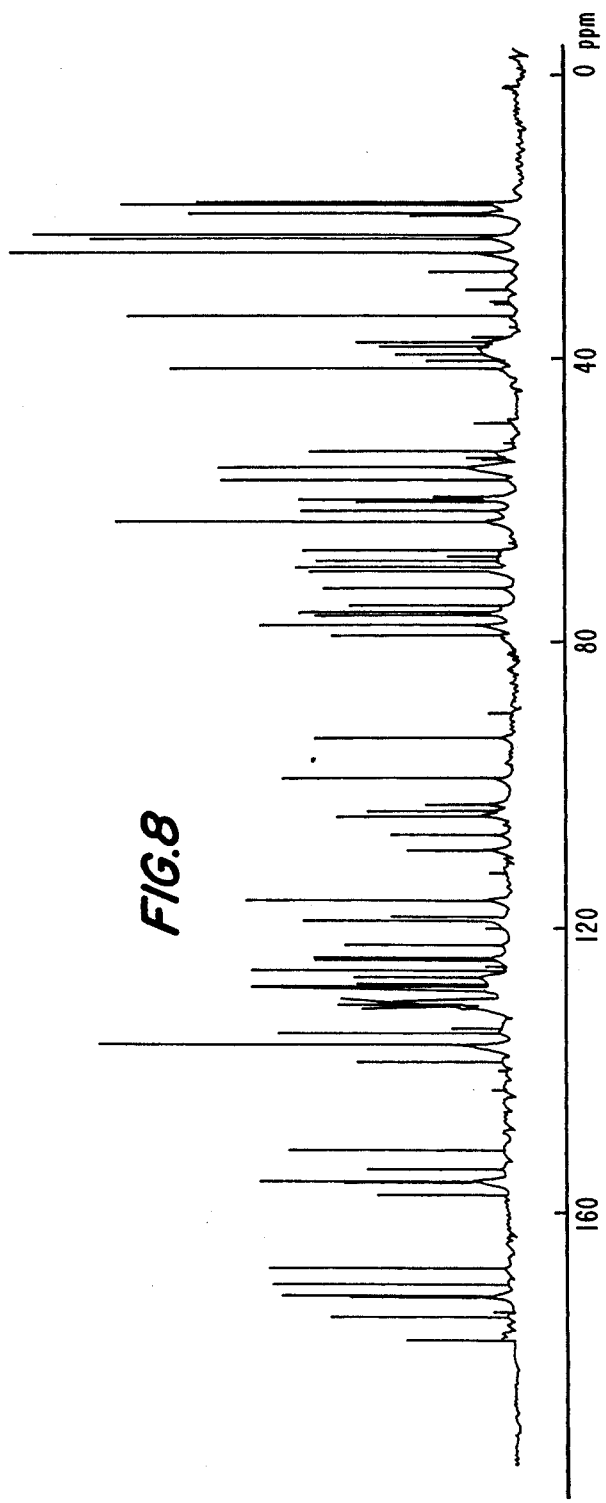

$^{13}$C-NMR: 50 MHz, in D$_2$O, external standard CH$_3$CN 1.7 ppm, 60° C., (see FIG. 8).

δ ppm: 177.9, 177.8, 174.8, 172.2, 172.1, 171.7, 170.3, 167.8, 157.6, 156.1, 156, 155.8, 155.5, 153.9, 151.2, 139, 137, 136.7, 136.7, 135, 134.2, 131.4, 130.9, 128.8, 128.4, 127.9, 127.1, 126.4, 124.5, 124.3, 124.1, 122.6, 119.3, 118.6, 109.3, 107.2, 104.6, 104, 102.9, 99.3, 93.7, 79.4, 78.1, 77.9, 76.7, 76.1, 75.2, 72.5, 70.2, 69.6, 68.7, 67.3, 63.1, 63.1, 61.7, 60.4, 59.9, 57.1, 55.5, 55.5, 53, 41.5, 40.2, 39.3, 37.7, 34.1, 25.1, 23.3, 22.5, 19.3, 18.3, 17.8.

Thin layer chromatography
Merck precoated TLC plate silica gel 60F254.
Developing solvent: chloroform:methanol:conc. ammonia water:sec-butanol:water (5:10:5:5:2).
Rf=0.22.

High performance liquid chromatography (Shimazu LC-6A)
Column: Nucleosil 5C18 $\phi$4.6×150 mm.
Detection: UV 220 nm.
Flow rate: 1 ml/min.
Mobile phase: 9% acetonitrile-0.05M phosphate buffer (pH3.5).
Retention time: 9.4 min.
Mobile phase: 10% acetonitrile-0.05M phosphate buffer (pH3.5).
Retention time: 6.9 min.
Color reaction: Ninhydrin positive
Solubility
Soluble in water and dimethylsulfoxide.
Slightly soluble in alcohol.
Insoluble in ether, benzene, chloroform and ethyl acetate.

Appearance
amphoteric, white amorphous powder.

From the above physicochemical properties, PA-42867-A and PA-42867-B are deduced to have the following configuration.

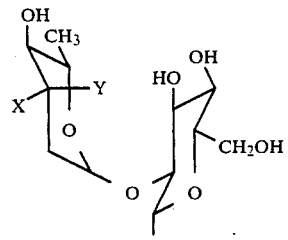

-continued

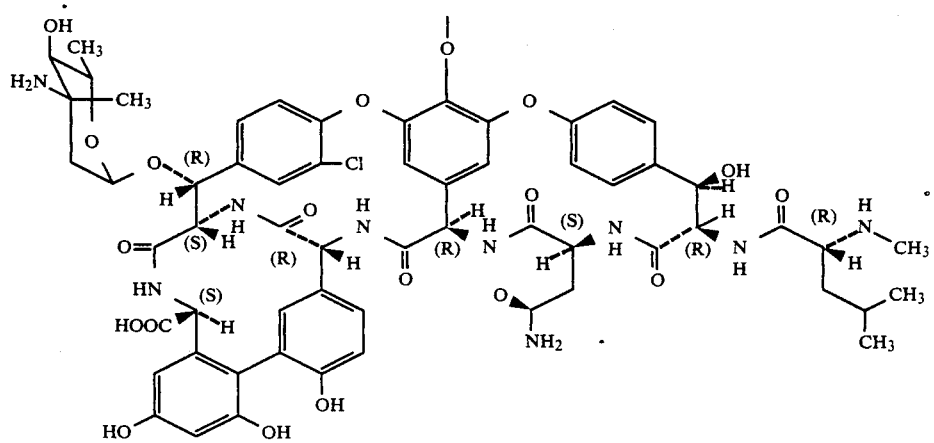

wherein X is NH₂ and Y is CH₃; or X is OH and Y is H.

PA-42867-A and PA-42867-B have the above-mentioned properties different from the conventional glycopeptide antibiotics and, therefore, are determined to be new glycopeptide antibiotics.

The strain PA-42867 isolated from a certain soil sample is exemplified as a microorganism producing PA-42867-A and PA-42867-B. It is determined to belong to *Nocardia orientalis* through taxological investigation and has been deposited as *Nocardia orientalis* PA-42867 (FERM BP-1230) with the Fermentation Research Institute Agency of the Industrial Science & Technology under the Budapest Treaty. This invention comprehends all of microorganisms producing PA-42867-A and/or -B as well as the strain PA-42867 or its natural or artificial mutants.

The strain has the following taxonomical characteristics.

(1) Morphological character

On Yeast-Malt agar, Tyrosine agar and Bennett's agar media, aerial mycelium and spore of this strain are formed abundantly. No whirl is observed. Aerial mycelium develops well and the spore chains are straight or wavy. The shape of spore is long cylindrical and 0.3–0.5×1.2–1.7 μm in size and the spore surface structure is smooth under electron microscopic observation. Neither sporangium, flagellated spore nor sclerotium is observed.

(2) Cultural characteristics (incubated at 28° C. for 14 days)

| Medium | Growth | Aerial mycelia Formation | Color | Substrate mycelia | Soluble pigment |
|---|---|---|---|---|---|
| Sucrose. nitrate agar | good | good | white | pale yellowish brown~pale yellow | pale yellow |
| Glucose. asparagine agar | good | none | — | pale yellow ~yellow | pale yellow |
| Glycerol. asparagine agar | good | good | white ~pale yellow | yellow | yellow |
| Inorganic salt. starch agar | good | good | white | pale yellowish brown | none |
| Tyrosine agar | good | good | pale yellow | pale yellow ~pale yellowish brown | none |
| Nutrient agar | good | none | — | pale yellowish brown | none |
| Yeast ext. Malt ext agar | good | good | white | pale yellow ~pale yellowish brown | yellow |
| Oatmeal agar | good | good | white | pale yellowish brown | none |
| Bennett's agar | good | good | white | pale yellow ~pale yellowish brown | yellow |

Colors are determined from GUIDE TO COLOR STANDARD (Japanese Color Institute).

GROWTH TEMPERATURE (incubated at each temperature for 14 days on Bennett's agar)

10° C.: Growth is fairly well and aerial mycelium is not formed.
28° C.: Growth and formation of aerial mycelia and spores are well.
37° C.: not growing.
45° C.: not growing.

(3) Physiological character (incubated at 28° C. for 14 days)

| | |
|---|---|
| Melanin production | negative |
| Tyrosinase reaction | negative |
| Coagulation of milk | negative |
| Peptonization of milk | positive |
| Gelatin liquefaction | positive |
| Starch hydrolysis | negative |

(4) Utilization of carbohydrates

| | |
|---|---|
| L-arabinose | − |
| D-xylose | + |
| D-glucose | + |
| D-fructose | + |
| Sucrose | − |
| Inositol | + |
| L-rhamnose | − |
| Raffinose | − |
| D-mannitol | + |
| Control (without sugar) | − |

+: well growing
−: not growing

(5) Cell Wall Composition

The diaminopimeric acid of this strain is of meso-form.

This strain is determined to belong to the genus Nocardia from the above characteristics.

The closest species to this strain was searched from the following literatures;

i. Waxman S.A.: The Actinomycetes, vol. 2 (1961),
ii. Elwood B. Shirling and David Gottlieb: International Journal of Systematic Bacteriology, vol. 18 (1968), vol. 19 (1969) and vol. 22 (1972),
iii. Bergy's Manual of Determinative Bacteriology, the eighth edition (1974), and
iv. Other literatures disclosing new species of Actinomycetes.

As a result, this strain was determined to belong to *Nocardia orientalis* (This is referred to as *Streptomyces orientalis* in the following literature; International Journal of Systematic Bacteriology vol. 18, 154–157 (1968) and The Actinomycetes, vol. 2, 254–255 (1961)). Compared with *Nocardia orientalis*, the main characteristics of this strain PA-42867 is identical with those of *Nocardia orientalis* except utilization of arabinose and rhamnose. Accordingly, this strain PA-42867 was identified as the species *Nocardia orientalis* and named *Nocardia orientalis* PA-42867.

All of strains belonging to the genus Nocardia and producing PA-42867-A and/or -B as well as the above strain PA-42867 and its natural or artificial mutants can be used and involved in this invention.

PA-42867-A and/or -B are prepared by incubating a PA-42867-A- and/or -B-producing strain in a nutrient broth under an aerobic condition and isolating and collecting PA-42867-A and/or -B from the incubated broth after the incubation. A general process for preparing PA-42867-A and/or -B is described below.

Composition and condition of broth generally used in preparing antibiotics can be applied to this process. The broth contains carbon sources, nitrogen sources and inorganic salts as a general rule. As occasion demands, vitamins, precursors and so on may be added to the broth. The carbon source such as glucose, starch, dextrin, glycerol, molasses, organic acids and the like may be employed alone or as a mixture. The nitrogen source such as soy bean meal, corn steep liquor, meat extract, yeast extract, cottonseed powder, peptone, wheat germ, ammonium sulfate, ammonium nitrate and the like may be employed alone or as a mixture. The inorganic acid such as calcium carbonate, sodium chloride, potassium chloride, magnesium sulfate, copper sulfate, manganese chloride, zinc sulfate, cobalt chloride, a kind of phosphates and the like may be added to the broth as occasion demands.

The fermentation can be achieved according to the general method for preparing antibiotics. In this invention, liquid culture, especially submerged aeration culture in a mass production, is preferable. In a case that pH of the broth alters, a buffer agent such as calcium carbonate is added to the broth. The preferable temperature of the fermentation is about 20–40° C., especially 28–32° C. The time of the fermentation deeply depends upon the scale of the fermentation and it takes about 60–100 hours to achieve mass fermentation. Where a lot of foam is induced during the fermentation, a defoamer such as vegetable oil, polypropylene glycol may properly be added thereto before or during the fermentation.

The isolation and collection of PA-42867-A and/or -B from the fermented broth after the fermentation can be performed according to the usual method for the isolation and collection of conventional fermentation products, for example, filtration, centrifugation, adsorption and desorption or chromatography by several kinds of ion exchange resins or other active adsorbents, extraction by several kinds of organic solvents and their combination.

The present inventors, after intensively accumulating studies with the purpose of developing novel antibiotics, have found that novel glycopeptide antibiotics possessing excellent antibacterial activity can be obtained selectively and at high yield by hydrolyzing said PA-42867-A and/or PA-42867-B in the presence of an acid.

That is, this invention is further to present a novel glycopeptide antibiotics represented by the formula III;

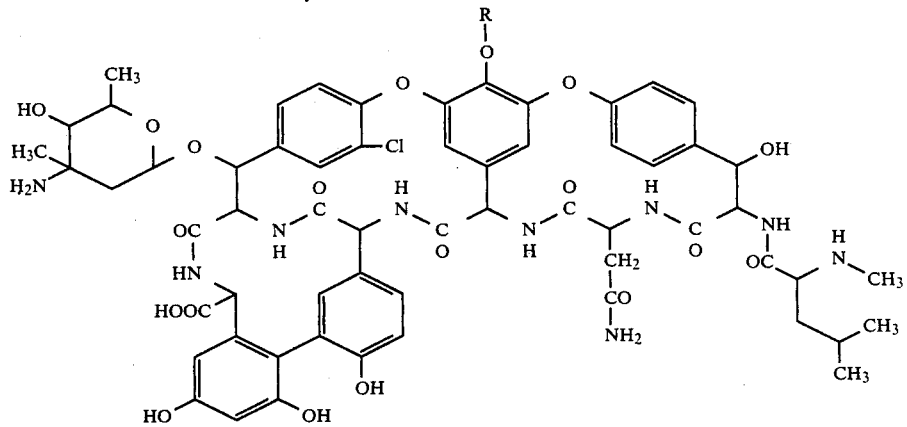

wherein R is

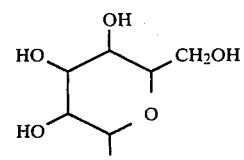

or H, or its pharmaceutically acceptable salt. More particularly, this invention is to present des-(4-epi-vancosaminyl) PA-42867-A where R is

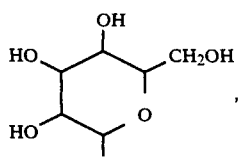

des-(4-epi-vancosaminyl-O-glucosyl) PA-42867-A where R is hydrogen, and their salts.

The physical properties of the compounds of formula III are shown below.

Figure 9:
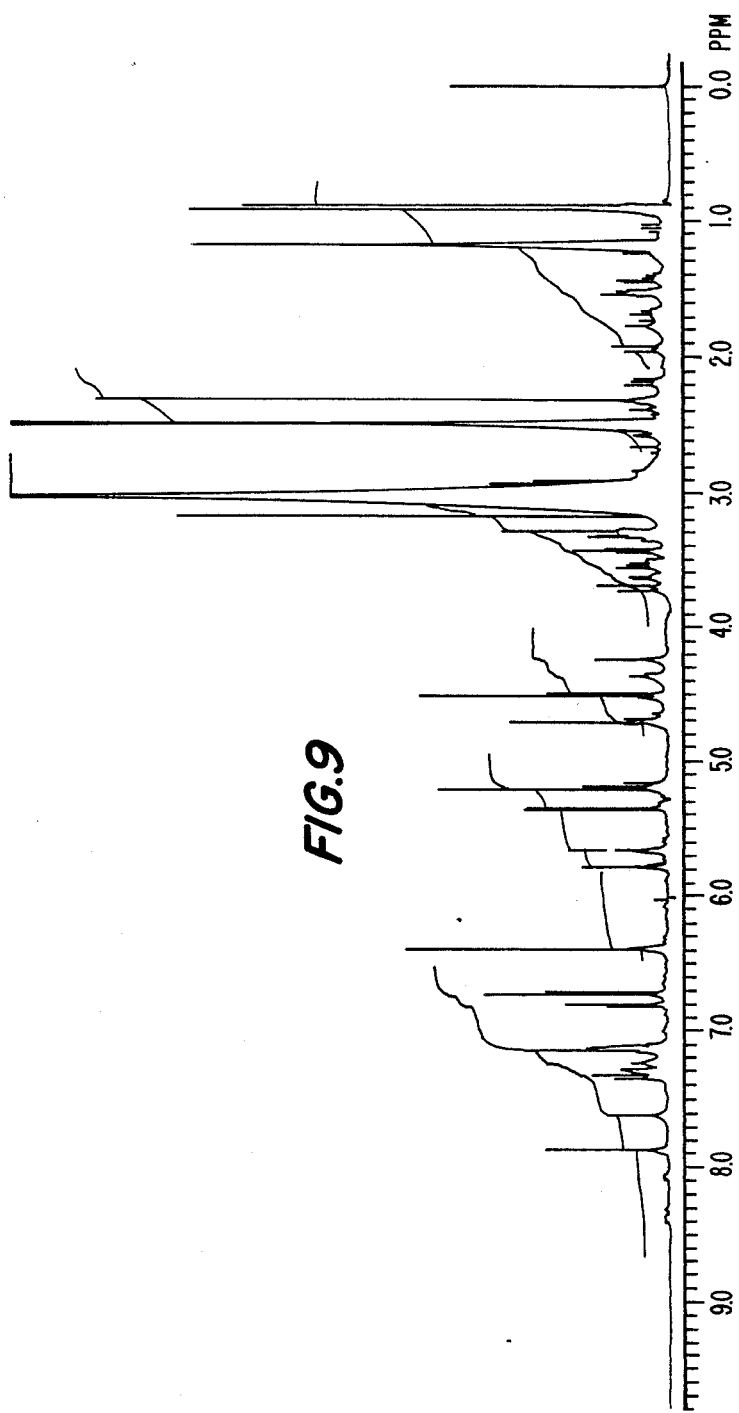
FIGS. 9 and 10 show $^1$H-NMR spectrum of des-(4-epi-vancosaminyl) PA-42867-A and des-(4-epi-vancosaminyl-O-glucosyl) PA-42867-A, respectively.

Des-(4-epi-vancosaminyl) PA-42867-A:
Specific rotatory power
$[\alpha]_D^{24°}$: $-91.5\pm3.1°$ (C=0.422, water).
IR spectrum
KBr, cm$^{-1}$: 3380, 2928, 1658, 1587, 1505, 1422, 1395, 1228, 1131, 1064, 1029, 1012, 1000.
Mass analysis (SIMS)
MS m/Z: 1414 (M+H)$^+$.
Circular dichroism spectrum (CD spectrum)
$\lambda_{max}^{0.05M\ PBS\ (pH3.5)}$nm [θ]:310 (0), 285 (−15400), 277 (sh) (−7300), 260 (−950), 251 (−1140), 249 (0), 228 (+127400), 214 (0).
NMR spectrum ($^1$H NMR) (see FIG. 9)
400 MHz, d$_6$-DMSO+D$_2$O (1 drop), 100° C., internal standard TMS
δ ppm: 0.889 (3H, d, J=6.7 Hz), 0.916 (3H, d, 6.5), 1.179 (3H, s), 1.179 (3H, d, 6.2), 1.427 (1H, d, d, d, 14.2, 7.8, 6.3), 1.529 (1H, d, d, d, 14.2, 7.6, 5.8), 1.670 (1H, d, d, 13.9 and 4.4) 1.763 (1H, m), 1.942 (1H, d-like, 13.9), 2.178 (1H, d, d, 16.0 and 7.3), 2.314 (3H, s), 2.549 (1H, d, d, 16.0, 5.2), 2.920 (1H, d, 9.7), approx. 3.3 (2H, m), 3.339 (1H, t, 8.7), 3.439 (1H, d, d, 7.3, 8.7), 3.542 (1H, d, d, 11.5 and 4.5), 3.634 (1H, q, d, 6.2 and 9.7), 3.711 (1H, d, d, 11.5 and 2.0), 4.238 (1H, br. s-like), 4.356 (1H, d, d, 7.3 and 5.2), 4.489 (1H, br. s). 4.519 (1H, s), 4.694 (1H, d-like, 4.4), 4.704 (1H, d, 4.0), 5.169 (1H, d-like, 4.0), 5.204 (2H, br. s-like), 5.346 (1H, d, 7.3), 5.659 (1H, br. s), 5.778 (1H, br. s), 6.380 (1H, d, 2.3), 6.394 (1H, d, 2.3), 6.723 (1H, d, 8.5), 6.806 (1H, d, d, 8.5 and 2.3), 7.104 (1H, d, d, 8.4 and 2.3), 7.135 (1H, d, d, 8.4 and 2.4), 7.151 (1H, d, 2.3), 7.228 (1H, br. d, 8.4), 7.294 (1H, d, d, 8.4 and 2.3), 7.338 (1H, d, d, 8.4 and 2.0), 7.602 (1H, d, d, 8.4 and 2.3), 7.864 (1H, d-like, 2.0)

Figure 10:
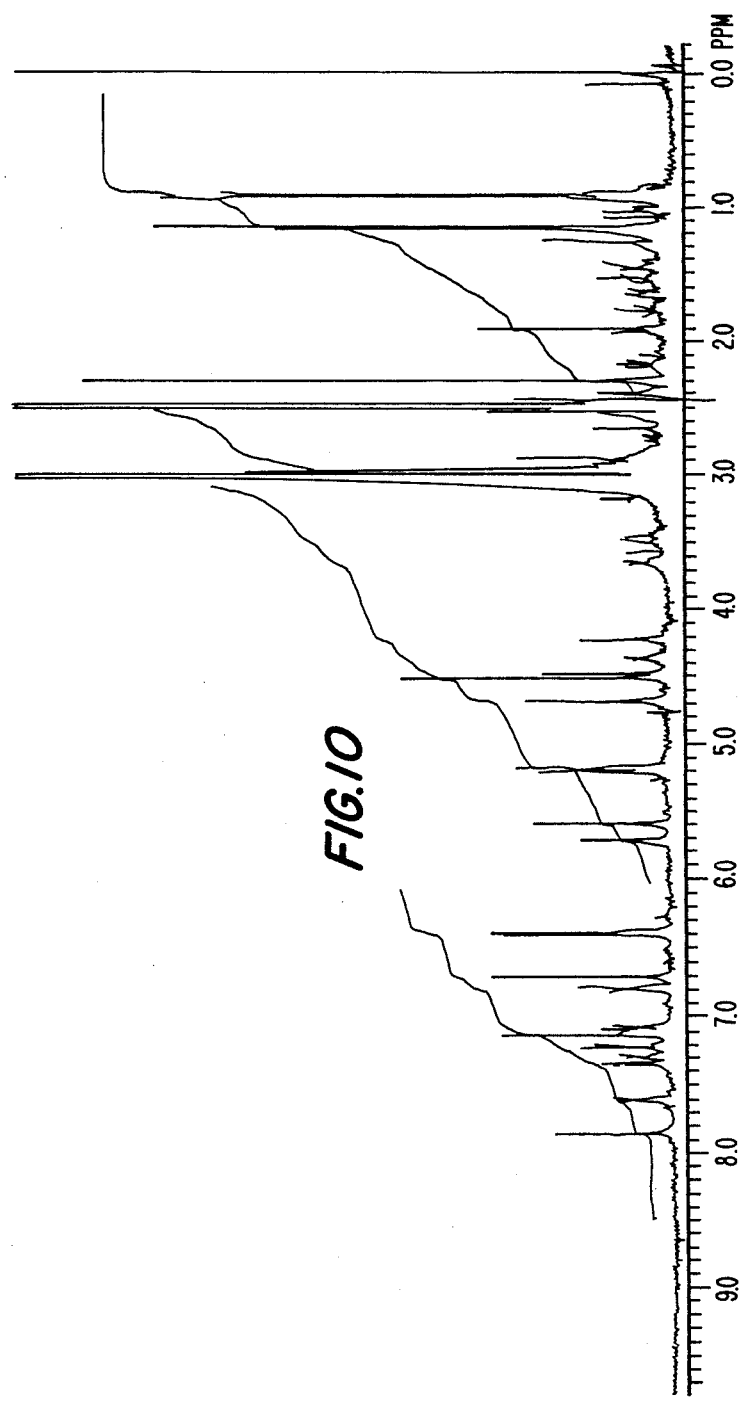

Des-(4-epi-vancosaminyl-O-glucosyl) PA-42867-A:
Specific rotatory power
$[\alpha]_D^{24°}$: $-62.0\pm4.9°$ (C=0.209, water).
IR spectrum
KBr, cm$^{-1}$: 3392, 2964, 1657, 1598, 1510, 1429, 1394, 1231, 1207, 1061, 1012, 1005.
Mass analysis (SIMS)
MS m/Z: 1252 (M+H)$^{30}$.
Circular dichroism spectrum (CD spectrum)
$\lambda_{max}^{0.05M\ PBS\ (pH3.5)}$nm[θ]: 310 (0), 284.5 (−17200), 264 (−2430), 250 (−11600), 246 (0), 225 (+139000), 213 (0).
NMR spectrum ($^1$H NMR) (see FIG. 10)
400 MHz, d$_6$-DMSO+D$_2$O (1 drop), 100° C. internal standard TMS.
δ ppm: 0.888 (3H, d, J=6.6 Hz), 0.915 (3H, d, 6.7), 1.142 (3H, s), 1.174 (3H, d, 6.1), 1.425 (1H, d, d, d, 14.0, 8.0, 6.5), 1.528 (1H, d, d, d, 14.0, 7.6, 5.7), 1.626 (1H, d, d, 13.7 and 4.4), 1.763 (1H, m), 1.910 (1H, d-like, 13.7), 2.173 (1h, d, d, 16.0 and 7.5), 2.304 (3H, s), 2.545 (1H, d, d, 16.0, 5.4), 2.874 (1H, d, 9.7), 3.653 (1H, qd, 6.1 and 9.7), 4.220 (1H, br. s-like), 4.359 (1H, d, d, 7.5 and 5.0), 4.475 (1H, br. s), 4.513 (1H, s), 4.686 (1H, br. d-like, 4.4), 4.689 (1H, d, 3.9), 5.175 (1H, d-like, 3.9), 5.184 (1H, d, d, 2.3 and 1.1), 5.206 (1H, br. s), 5.598 (1H, br. s), 5.723 (1H, br. s), 6.378 (1H, d, 2.3), 6.401 (1H, d, 2.3), 6.709 (1H, d, 8.5), 6.794 (1H, d, d, 8.5 and 2.3), 7.074 (1H, d, d, 8.4 and 2.4), 7.119 (1H, d, d, 8.4 and 2.4), 7.130 (1H, d, 2.3), 7.215 (1H, d, 8.4), 7.288 (1H, d, d, 8.4 and 2.2), 7.342 (1H, d, d, 8.4 and 2.0), 7.601 (1H, d, d-like, 8.4 and 2.2), 7.848 (1H, d, 2.0).

Estimating from the above physicochemical properties, des-(4-epi-vancosaminyl) PA-42867-A and des-(4-epi-vancosaminyl-O-glucosyl) PA-42867-A are considered to have the following configuration.

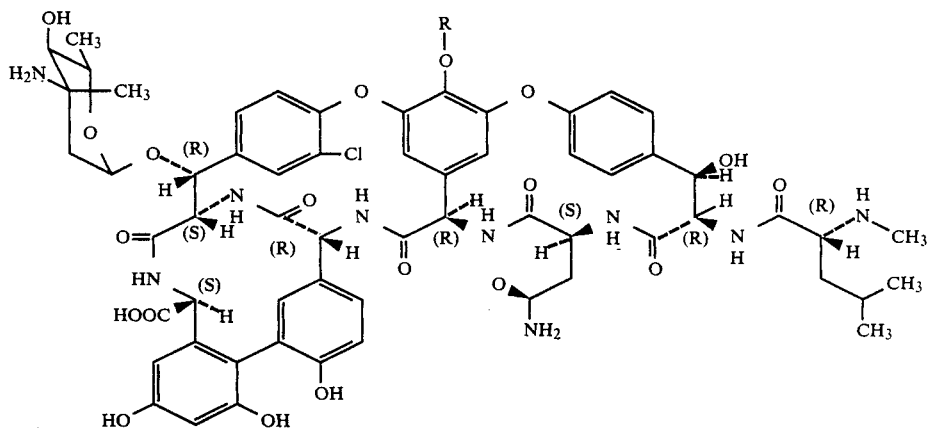

Des-(4-epi-vancosaminyl) PA-42867-A:
(Molecular weight 1414.8 calcd. for C$_{66}$H$_{76}$O$_{24}$N$_9$Cl)
R:

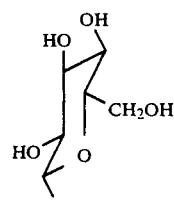

Des-(4-epi-vancosaminyl-O-glucosyl) PA-42867-A:
(Molecular weight 1252.7 calcd. for C$_{60}$H$_{66}$O$_{19}$N$_9$Cl)
R:H These compounds are manufactured from the starting substance PA-42867-A or PA-42867-B represented by the formula II or their mixture, according to the following reaction scheme:
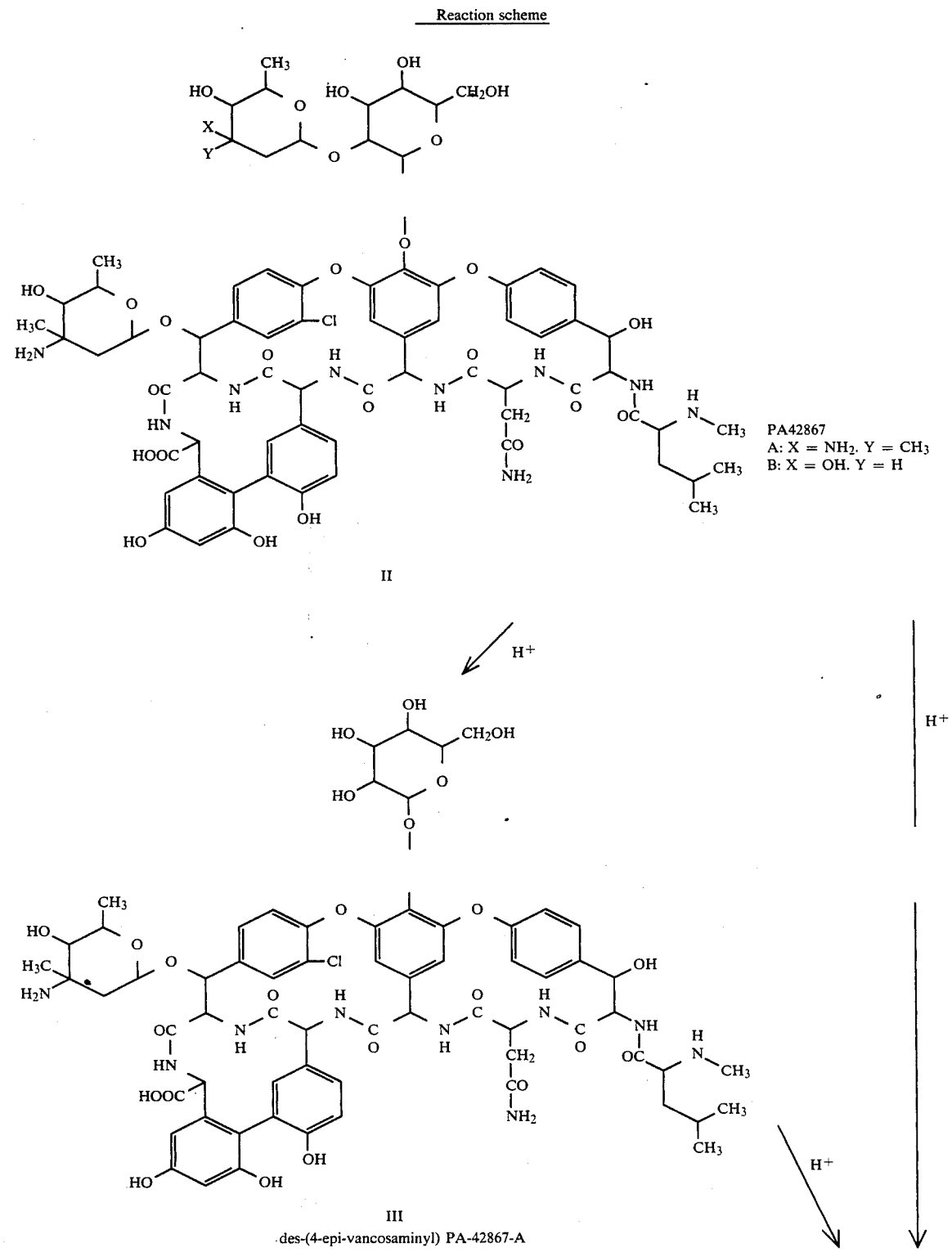
Reaction scheme
PA42867
A: X = NH$_2$, Y = CH$_3$
B: X = OH, Y = H
II
III
des-(4-epi-vancosaminyl) PA-42867-A -continued
Reaction scheme

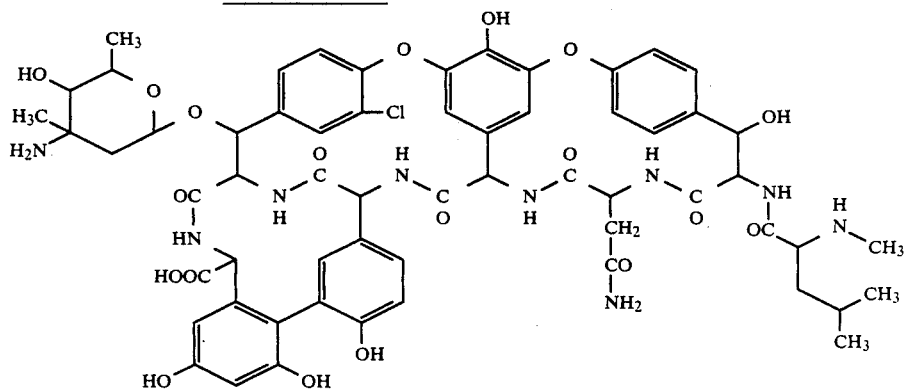

III
des-(4-epi-vancosaminyl-O-glucosyl) PA-42867-A

In the above reaction, the starting substance may be either PA-42867-A or PA-42867-B, but it is more advantageous to use a crude product containing the both which is obtained in their manufacturing processes.

When the starting substance represented by the formula II PA-42867 (A or B or their mixture) is hydrolyzed in an acid, two compounds of this invention represented by the formula III are produced. As clear from the reaction scheme, des-(4-epi-vancosaminyl) PA-42867-A is produced when only the 4-epi-vancosaminyl group of the side chain of PA-42867-A or the olivosyl group of the side chain of PA-42867-B is hydrolyzed. On the other hand, des-(4-epi-vancosaminyl-O-glucosyl) PA-42867-A is obtained by hydrolyzing a product from which only this 4-epi-vancosaminyl or olivosyl group is cut off and removing the sugar residue, or by simultaneously removing these 4-epi-vancosaminyl or olivosyl group and sugar residue from the compound in formula II. It is also possible to produce desired products selectively by properly selecting the reaction conditions (acid concentration, temperature, time, etc.). Generally the reaction products obtained by carrying out the reaction in proper conditions can be isolated and refined according to the usual process for isolating and refining ordinary antibiotics known in this field to give the individual compound.

According to the method of hydrolyzing in an acid of this invention, novel glycopeptide antibiotics represented in the formula III may be obtained easily at high yield.

An acid used in this invention includes inorganic acids such as hydrochloric acid and sulfuric acid, and organic acids such as trifluoroacetic acid. The reaction conditions, such as acid concentration, solvent, reaction temperature and reaction time generally conform to the conditions under which sugar chains of glycopeptide antibiotics are usually hydrolyzed. When said acids are used, it is enough to react for 10 minutes to 24 hours at 0° to 50° C. The acid concentration varies with each acid, for example, 5 to 36% for hydrochloric acid, 2N to 12N for sulfuric acid, and 30 to 100% for trifluoroacetic acid. The reaction is preferably conducted in a nitrogen atmosphere.

As a result of the above reaction, a mixture of des-(4-epi-vancosaminyl)PA-42867-A and des-(4-epi-vancosaminyl-O-glucosyl) PA-42867-A represented by the formula III is obtained, but one of these compounds may be selectively produced depending on the reaction conditions. To selectively produce des-(4-epi-vancosaminyl)PA-42867-A, it is enough to react with about 20% of hydrochloric acid at about 0° to 1° C. for about 15 to 20 hours, with 5 to 10N of sulfuric acid at room temperature for about 1 to 5 hours, or with about 70 to 100% of trifluoroacetic acid at about 25° to 35° C. for about 10 minutes to 2 hours. To selectively produce des-(4-epi-vancosaminyl-O-glucosyl)PA-42867-A, it is enough to react with about 80% of trifluoroacetic acid at about 40° to 50° C. for about 2 to 4 hours. In the above reaction conditions, either compound is produced at a yield of nearly over 70%.

In the next step, the obtained reaction mixture is neutralized with a base such as sodium hydroxide, applied to column chromatography using adsorbent such as MCI GEL CHP-20P (Mitsubishi Chemical Industries Co., Ltd.) and fractioned with various eluents, and fractions with high contents of products are collected by high performance liquid chromatography (HPLC). By repeating the fractionation as required, solutions containing each product at high purity can be obtained, and desired products are precipitated by methanol sedimentation or other process, and this sediment is recrystallized from methanol-water. On the other hand, the filtrate mother liquor is freeze-dried to obtain the freeze-dried product.

In this method, compounds of the formula III with HPLC purity of about 91% or higher can be obtained at a high yield of about 50 to 74%.

The compounds of the formula I may directly be used in treatment of humans and animals, but is may often be desired to be prepared in a form of salt in terms of absorption into the body. Examples of bases capable of forming a salt with the compounds of this invention include alkaline metals such as potassium and sodium; alkaline earth metals such as aluminium and magnesium, and examples of acid may include inorganic acids such as hydrochloric acid, sulfuric acid and nitric acid, and organic acids such as acetic acid and fumaric acid.

The compounds and their salts of this invention can be administered to humans and animals either orally or parenterally as activve ingredients of antibacterial agent. They may be administered in the oral route in the form of tablet, capsule or powder by using widely applied vehicles, stabilizers, preservatives, wetting agents, surfactants or the like, or in parenteral routes in the form of injection, ointment or suppository. The dose varies with the purpose of treatment and the age and condition of patients, but generally in the case of intravenous injection a daily dose is about 0.1 to 10 g in an adult patient.

The compounds of this invention show potent antimicrobial activity against gram-positivve bacteria, especially methicillin-resistant bacteria, so that they are useful as human and veterinary medicine. And they are suitable for injectable preparation as well as oral preparation since they can highly be purified.

EXAMPLE

This invention is further explained in more detail in but not restricted by the following example.

EXAMPLE 1

(a) Fermentation step

Seed slant culture of Nocardia sp. PA-42867 (FERM BP-1230) is inoculated into an Erlenmeyer flask (2 L) charged with 800 ml of the broth comprising 0.5% soluble starch, 0.5% glucose, 0.5% polypeptone, 0.5% meat ext., 0.25% yeast ext., 0.25% sodium chloride and deionized water (pH 7.0 before sterilization) and fermented with shaking at 180 r.p.m. at 28° C. for 48 hours. This fermented broth (800 ml) is transplanted into a jar-fermenter (30 L) charged with 20 L of the same broth as noted above and fermented at 28° C. for 24 hours with stirring at 200 r.p.m. (aeration rate 20 L/min. and internal pressure 0.5 $Kg/cm^2G$). Then, 10 L of the resulting broth is transplanted into a fermentation tank (250 L) charged with 140 L of the broth comprising 2.4% tomato paste, 2.4% dextrin, 1.2% dried yeast (Iwaki Seiyaku Co., Ltd.), 0.0006% cobalt chloride hexahydrate, 0.08% defoamer P-2000 (Dai Nippon Ink & Chemicals Inc.) and water (pH 7.0 before sterilization) and fermented at 28° C. for 64 hours with stirring at 325 r.p.m. (aeration rate 150 L/min. and internal pressure 5 p.s.i.).

(b) Isolation step

The fermented broth prepared in the above step, which is adjusted to pH 10.5 with 10% sodium hydroxide, is centrifuged to give 145 L of the supernatant. Adjusted to pH 4.0, the supernatant is applied to a column charged with 13 L of Dowex 50×2 ($Na^+$ type) (The Dow chemical Co.), washed with 70 L of water and eluted with 40 L of 30% acetone water containing 1% triethylamine. The fractions showing activity by the pulp disc dispersion method employing Bacillus subtilis are collected. (22 L), adjusted to pH 5.0 and condensed by evaporating acetone under reduced pressure. The resultant is applied to a column of 2 L of HP-20 (Mitsubishi Chemical Industries Co., Ltd.), washed with 20 L of water and eluted with 50% acetone water. The active fractions are collected (6 L), condensed under reduced pressure and lyophilized to give the crude powder 35.6 g of PA-42867.

(c) Purification Step

The above crude powder (12 g) is dissolved in 150 ml of 0.01N hydrochloric acid and applied to a column of 100 ml of MCI GEL CHP-20P (Mitsubishi Chemical Industries Co.), followed by eluted with 0.01N hydrochloric acid as tracing out the content of PA-42867 with HPLC. The fractions containing PA-42867-A and -B are adjusted to pH 7.0 and chromatographed again with CHP-20P: the fractions containing PA-42867-A and -B are applied to the column, washed well with 15% methanol water, and eluted with 15% methanol-0.005N hydrochloric acid to give the fraction containing PA-42867-A and the fraction containing PA-42867-B.

The fraction containing PA-42867-A is adjusted to pH 7.0 and condensed. For the purpose of decoloration, the resultant is applied to a column of 10 ml of CHP-20P and eluted with dilute hydrochloric acid (pH 5.0) to give the fraction containing PA-42867-A, which is condensed and lyophilized to give 571 mg of the residue (70% purity). After 571 mg of this residue is dissolved in water and ajusted to pH 5.0 by adding dilute hydrochloric acid, the solution is applied to a column of 10 ml of CHP-20P and eluted with water to give the fraction of PA-42867-A, which is adjusted to pH 7.0 and condensed. The resultant is applied again to a column of 10 ml of CHP-20P (stabilized with 0.05M phosphate buffered saline (pH 7.0)) for the purpose of desalting, washed with 0.05M phosphate buffered saline (pH 7.0) and then with water and eluted with 50% methanol water to give the fraction of PA-42867-A, which is condensed and lyophilized to give 256 mg of PA-42867-A (95% purity).

The fraction containing PA-42867-B as noted above is adjusted to pH 7.0, condensed with lyophilized to give 683 mg of the residue. The residue (683 mg) of PA-42867-B dissolved in water is adjusted to pH 4.0 by adding dilute hydrochloric acid, applied to a column of 5 ml of CHP-20P for the purpose of decoloration and eluted with dilute hydrochloric acid (pH 4.0) to give the fraction of PA-42867-B, which is adjusted to pH 7.0 and condensed. The resultant is applied to Packed Column RQ-2 (Fujigeru Hanbai K.K.) and eluted with 7% acetonitrile-0.05M phosphate buffered saline (pH 4.9) and then 8% acetonitrile-0.05M phosphate buffered saline (pH 4.9) as the purity of PA-42867-B is traced with HPLC. The fractions showing more than 95% purity are collected, adjusted to pH 7.0 and condensed. The resultant is applied to a column of 10 ml of CHP-20P (stabilized with 0.05M phosphate buffered saline (pH 7.0)) for desalting, washed with water and eluted with 50% methanol water to give the fractions containing PA-42867-B, which are condensed and lyophilized to give 102 mg of PA-42867-B (98% purity).

EXAMPLE 2

Precisely 2.00 g of crude product obtained in the above step (b) of example 1 (containing 53% of PA-42867-A and 9% of PA-42867-B) is dissolved in 200 ml of 20% hydrochloric acid (Wako Pure Chemical Industries, Ltd., for precision analysis) and stirred with ice-chilled (0° to 1° C.) under nitrogen atmosphere for 16 hours. To the reaction solution, 6N sodium hydroxide (about 204 ml) is added to adjust to pH 9.2. It is applied to MCI GEl CHP-20P (200 to 400 mesh, 100 ml), and is eluted with successive, water (600 ml), 0.01N hydrochoric acid (450 ml), water (450 ml), 25% methanol water (450 ml), 50% methanol water (400 ml), methanol (400 ml) and 50% methanol-0.005N hydrochloric acid (400 ml).

By the fraction check with HPLC (Nucleosil 300-7C18, 4.6φ×250 mm, 10% acetonitrile-0.05M PBS (pH 3.5), flow rate 1 ml/min., 220 nm UV detection,) fraction A (0.01N hydrochloric acid- and water-elution portions) and fraction B (50% methanol-, methanol- and 50% methanol-0.005N hydrochloric acid-elution portion) are obtained.

Fraction B is concentrated, adjusted to pH 3.5, applied to MCI GEL CHP-20P (200 to 400 mesh, 10 ml) and eluted with successive, 300 ml of water (adjusted to pH 4.0 by hydrochloric acid water, about $10^{-4}$N hydrochloric acid), 100 ml of 15% methanol-water (pH 4.0), 100 ml of 30% methanol-water (pH 4.0), 100 ml of 50% methanol-water (pH 4.0), 50 ml of methanol and 50 ml of 50% methanol-0.005N hydrochloric acid to obtain fraction C (water (pH 4.0)-elution portion) and fraction D (50% methanol-water (pH 4.0)-elution portion).

Fractions A annd C are put together, concentrated, adjusted to pH 7.0 and desalted by using MCI GEL CHP-20P (200 to 400 mesh, 10 ml); eluted with successive, water (100 ml), 25% methanol water (100 ml), 50% methanol water (100 ml), methanol (100 ml) and 50% methanol-0.005N hydrochloric acid (50 ml) to obtain fraction E (not-desalted portion) and fraction F (desalted portion). Fraction E (not-desalted portion) is desalted again in the same condition to obtain fraction G (desalted portion).

In water (39 ml) is dissolved 800 mg of the sediments of obtained fractions F and G (after concentrating each fraction, methanol is added thereto to form sediment) with heating and methanol (39 ml) is added thereto for recrystallization to obtain 557 mg of crystals (drying under reduced pressure for 1.5 hour at 30° C. in the presence of phosphorus pentoxide) of des-(4-epi-vancosaminyl) PA-42867-A (HPLC 93% purity, yield 46.0%).

Separately, from crystal mother liquor and sediment forming mother liquor, 350 mg of freeze-dried product is obtained (des-(4-epi-vancosaminyl) PA-42867-A, HPLC 91% purity, yield 28.3%).

By similarly desalting fraction D, 30 mg of freeze-dried product is obtained (des-(4-epi-vancosaminyl-O-glucosyl) PA-42867-A, HPLC 93% purity, yield 2.8%).

EXAMPLE 3

Precisely 100 mg of PA-42867-A of 90% purity obtained in the same manner as in the above step (c) of example 1 is dissolved in 10 ml of 20- hydrochloric acid and stirred for 10 minutes with heating in an oil bath at 40° to 45° C. under a nitrogen atmosphere. The reaction solution is adjusted to pH 9.2 with 6N NaOH, applied to MCI GEL CHP-20P (200 to 400 mesh, 10 ml) and eluted with successive, water (100 ml), 0.01N hydrochloric acid (50 ml), water (50 ml), 25% methanol (50 ml), 50% methanol (50 ml), methanol (50 ml) and 50% methanol-0.005N hydrochloric acid (50 ml). By checking the fraction with HPLC (Nucleosil 300-7C18, 10% acetonitrile-0.05M PBS (pH 3.5), 220 nm UV detection), fraction I (0.01N hydrochloric acid- and water-elution portions) and fraction II (50% methanol-, methanol- and 50% methanol-0.005N hydrochloric acid-elution portions) are obtained.

Fraction II is concentrated, adjusted to pH 3.5, applied to MCI GEL CHP-20P (200 to 400 mesh, 10 ml) and eluted with successive, 50 ml of water (pH 4.0), 15% methanol-water (pH 4.0), 30% methanol-water (pH 4.0), 50% methanol-water (pH 4.0), 50 ml of methanol and 50 ml of 50% methanol-0.005N hydrochloric acid to obtain fraction III (water pH 4.0)-elution portion) and fraction IV (50% methanol-water (pH 4.0)- and 50% methanol-0.005N hydrochloric-elution portions).

Fractions I, III are put together, concentrated, adjusted to pH 7.0 and desalted by using MCI GEL CHP-20P (200 to 400 mesh, 5 ml) to obtain des-(4-epi-vancosaminyl) PA-42867-A by 31.5 mg (yield 38.6%).

Fraction IV is similarly desalted to give 36.3 mg (yield 50.1%) of des-(4-epi-vancosaminyl-O-glucosyl) PA-42867-A.

EXAMPLE 4

Refined PA-42867-A is hydrolyzed in hydrochloric acid, sulfuric acid or trifluoroacetic acid under the reaction conditions shown in Table 1 in order to find out the reaction condition under which one of des-(4-epi-vancosaminyl) PA-42867-A and des-(4-epi-vancosaminyl-O-glucosyl) PA-42867-A is selectively produced. The results are shown in Table 1.

As clear from Table 1, when the reaction conditions are properly selected, one of the compounds can be selectively produced at a yield of 70% or higher.

TABLE 1-1

| | Hydrocloric Acid | | | |
|---|---|---|---|---|
| Concentration | Temperature | Time | Yield (%) | |
| (%) | (°C.) | (hours) | Compd. 1 | Compd. 2 |
| 6 | 26 | 7 | 60 | — |
| 20 | 26 | 2 | 43 | 36 |
| 20 | 0 | 16 | 75 | 3 |
| 20 | 32 | 1 | 29 | 41 |
| 20 | 42 | 0.5 | 36 | 47 |
| 80 | 32 | 1 | 69 | 16 |
| 80 | 43–45 | 0.5 | 59 | 40 |
| 80 | 43–45 | 3 | 8 | 74 |

TABLE 1-2

| | Sulfuric Acid | | | |
|---|---|---|---|---|
| Concentration | Temperature | Time | Yield (%) | |
| (N) | (°C.) | (hours) | Compd. 1 | Compd. 2 |
| 6 | 26 | 4 | 61 | 8 |
| 9 | 26 | 2 | 76 | 7 |

TABLE 1-3

| | Trifluroacetic Acid | | | |
|---|---|---|---|---|
| Concentration | Temperature | Time | Yield (%) | |
| (%) | (°C.) | (hours) | Compd. 1 | Compd. 2 |
| 100 | 26 | 0.5 | 73 | 9 |
| 80 | 26 | 2 | 54 | 8 |
| 80 | 32 | 1 | 69 | 16 |
| 80 | 43–45 | 0.5 | 59 | 40 |
| 80 | 43–45 | 3 | 8 | 74 |

Compound 1: Des-(4- epi -vancosaminyl) PA-42867-A
Compound 2: Des-(4- epi -vancosaminyl-0-glucosyl) PA-42867-A

EFFECTS OF THE INVENTION

The in vitro and in vivo antibacterial activities of the compounds of this invention were evaluated in the following experimental examples.

EXPERIMENTAL EXAMPLE 1

In vitro antibacterial activity was determined by the agar dilution method as described below.

① Preparation of Bacterial Suspension

One loopful of each test bacterium on a slant was inoculated into 1 ml of a growth medium (Trypto Soy Broth, Eiken Chemical Co.) and incubated at 37° C. for 18–20 hours. For the growth of Streptococci, Mueller-Hinton broth (Difco) supplemented with 3%(V/V) horse serum was employed. A hundred-fold dilution of the culture is used as an inoculum suspension of the bacterium.

② Sample Solution

The sample (9–10 mg) was weighed and dissolved in distilled water at a concentration of 2 mg/ml.

③ Agar Plate

A sample solution was subjected to serial two fold dilutions with sterile water (2000–0.25 μg/ml). To sterile plastic petri dishes (9 cm in diameter) was poured 0.5 ml-aliquot of sample solutions, which was mixed with 9.5 ml of an agar medium (Sensitivity Test Agar, "Nissui"). For Streptococci, horse serum was supplied at 0.5%(V/V).

④ Measurement of MIC Value

One loopful (1.0 μl) of the inoculum suspension was placed on the surface of the agar plates prepared as noted above. The bacterial growth was examined visually after overnight incubation (18–20 hrs) at 37° C. The lowest concentration, at which bacterial growth is completely inhibited, is determined to be MIC (minimal inhibitory concentration).

The results are shown in Table 2.

TABLE 2

Antibacterial Activity Against Gram-Positive Organisms

| | MIC (μg/ml) | | | |
|---|---|---|---|---|
| Test organism | Compd. A | Compd. B | Compd. C | Compd. D |
| Staphylococcus aureus FDA 209F JC-1 · | 0.39 | 1.56 | 0.78 | 0.78 |
| Staphylococcus aureus ATCC 25923 | 0.78 | 3.13 | 1.56 | 1.56 |
| Staphylococcus aureus SMITH | 0.78 | 3.13 | 1.56 | 0.78 |
| Staphylococcus aureus SR14** | 0.78 | 1.56 | 1.56 | 0.78 |
| Staphylococcus aureus 3131* | 0.78 | 1.56 | 1.56 | 0.78 |
| Staphylococcus aureus SR1626* | 0.78 | 1.56 | 1.56 | 0.78 |
| Staphylococcus aureus SR3626* | 0.78 | 1.56 | 1.56 | 0.78 |
| Streptococcus pyogenes C-203 | 0.39 | 0.78 | 0.78 | 0.39 |
| Streptococcus pneumoniae Type I | 0.39 | 0.78 | 0.78 | 0.78 |
| Streptococcus agalactica SR1247 | 0.39 | 0.78 | 0.78 | 0.78 |
| Streptococcus faecalis SR1004 | 1.56 | 3.13 | 1.56 | 0.78 |
| Micrococcus luteus ATCC 9341 | 0.39 | 1.56 | 0.78 | 0.78 |

Compd. A: PA-42867-A
Compd. B: PA-42867-B
Compd. C: des-(4- epi -vancosaminyl) PA-42867-A
Compd. D: des-(4- epi -vancosaminyl-0-glucosyl) PA-42867-A
*methicillin resistant.
**penicillin resistant

EXPERIMENTAL EXAMPLE 2

In vivo antibacterial activity of PA-42867-A and des-(4-epi-vancosaminyl) PA-42867-A Method: Test bacterium is intraperitoneally challenged to Slc-ICR female mice (8 mice/group), to which PA-42867-A and des-(4-epi-vancosaminyl) PA-42867-A (serial two fold dilution) are subcutaneously administered 1 and 5 hours post-infection.

Result: $ED_{50}$ (50% effective dose) is calculated from survival rate of mice on day 7 after the infection.

The results are shown in Table 3.

TABLE 3

Antibacterial Activity by Protective Test in Mice

| | $ED_{50}$ (mg/kg/dose) | |
|---|---|---|
| Test organism | Compd. A | Compd. C |
| Staphylococcus aureus SMITH | 0.62 | 1.47 |
| Staphylococcus aureus SR2030* | 2.31 | 2.91 |
| Streptoccus pyogenes C-302 | 0.64 | 1.43 |

TABLE 3-continued

Antibacterial Activity by Protective Test in Mice

| | $ED_{50}$ (mg/kg/dose) | |
|---|---|---|
| Test organism | Compd. A | Compd. C |
| Streptococcus pneumoniae Type I | 0.90 | 2.11 |

Compd. A: PA-42867-A
Compd. C: des-(4- epi -vancosaminyl) PA-42867-A
*Methicillin-resistant organism

What we claim is:

1. An antibiotic represented by the following formula I;

[Chemical structure of formula I]

wherein R is

[Chemical structures]

or H, wherein X is $NH_2$ and Y is $CH_3$; or X is OH and Y is H, and its pharmaceutically acceptable salt.

2. The antibiotic of the claim 1, wherein R is

[Chemical structure]

wherein X is $NH_2$ and Y is $CH_3$.

3. The antibiotic of the claim 1, wherein R is

[Chemical structure]

wherein X is OH and Y is H.

4. The antibiotic of the claim 1, wherein R is

[Chemical structure]

5. The antibiotic of the claim 1, wherein R is H.

* * * * *